(12) United States Patent
Ise

(10) Patent No.: US 10,471,158 B2
(45) Date of Patent: Nov. 12, 2019

(54) N-ACETYLGLUCOSAMINE SUGAR CHAIN GROUP-CONTAINING COMPOUND, CARRIER COMPOUND FOR DRUG DELIVERY, DRUG PREPARATION, AND DRUG DELIVERY SYSTEM

(71) Applicant: SOMAR CORPORATION, Tokyo (JP)

(72) Inventor: Hirohiko Ise, Fukuoka (JP)

(73) Assignee: SOMAR CORPORATION, Tokyo (JP)

( * ) Notice: Subject to any disclaimer, the term of this patent is extended or adjusted under 35 U.S.C. 154(b) by 0 days.

(21) Appl. No.: 15/312,507

(22) PCT Filed: May 19, 2015

(86) PCT No.: PCT/JP2015/064344
§ 371 (c)(1),
(2) Date: Nov. 18, 2016

(87) PCT Pub. No.: WO2015/178380
PCT Pub. Date: Nov. 26, 2015

(65) Prior Publication Data
US 2017/0095564 A1 Apr. 6, 2017

(30) Foreign Application Priority Data
May 21, 2014 (JP) .................................. 2014-104811

(51) Int. Cl.
| | | |
|---|---|---|
| A61K 49/00 | (2006.01) | |
| A61K 47/36 | (2006.01) | |
| C08F 12/26 | (2006.01) | |
| A61K 41/00 | (2006.01) | |
| A61K 47/50 | (2017.01) | |
| A61K 47/54 | (2017.01) | |
| A61K 47/61 | (2017.01) | |
| A61K 47/69 | (2017.01) | |

(52) U.S. Cl.
CPC .......... *A61K 49/0052* (2013.01); *A61K 41/00* (2013.01); *A61K 47/36* (2013.01); *A61K 47/50* (2017.08); *A61K 47/542* (2017.08); *A61K 47/545* (2017.08); *A61K 47/549* (2017.08); *A61K 47/61* (2017.08); *A61K 47/6905* (2017.08); *A61K 49/00* (2013.01); *A61K 49/0043* (2013.01); *A61K 49/0076* (2013.01); *C08F 12/26* (2013.01)

(58) Field of Classification Search
CPC ........ A61K 47/48561; A61K 47/48384; A61K 49/0043; A61K 49/0058
See application file for complete search history.

(56) References Cited

U.S. PATENT DOCUMENTS

| | | | | |
|---|---|---|---|---|
| 5,206,318 A | * | 4/1993 | Kobayashi | ............. C07H 15/04 526/238.2 |
| 6,677,164 B1 | * | 1/2004 | Thoma | ................. C07K 1/1077 436/546 |
| 2005/0245735 A1 | * | 11/2005 | DeFrees | ................. A61K 45/06 536/53 |
| 2006/0052309 A1 | | 3/2006 | Ferguson et al. | |
| 2014/0058062 A1 | * | 2/2014 | Kajihara | ............... C07K 1/006 530/322 |

FOREIGN PATENT DOCUMENTS

| | | | |
|---|---|---|---|
| JP | 3-47802 A | | 2/1991 |
| JP | 8-320321 A | | 12/1996 |
| JP | H08320321 A | * | 12/1996 |
| JP | 2005-535674 A | | 11/2005 |
| JP | 2007-1923 A | | 1/2007 |
| JP | 2007001923 A | * | 1/2007 |
| JP | 2009-46413 A | | 3/2009 |
| JP | 2013-63926 A | | 4/2013 |

OTHER PUBLICATIONS

Aso et al., "Effective uptake of N-acetylglucosamine-conjugated liposomes by cardiomyocytes in vitro", Journal of Controlled Release, 2007, 122, pp. 189-198.
International Search Report, issued in PCT/JP2015/064344 (PCT/ISA/210), dated Aug. 25, 2015.
Ise et al., "N-acetylglucosamine Gar'yu Tosa Kobunshi PV-GlcNAc o Mochiita Saibo Kino Seigyo", Dai 33 Kai The Annual Meeting of the Japanese Society for Biomaterials Yokoshu, 2011, p. 148.
Ise et al., "Targeting N-acetylglucosamine-bearing polymer-coated liposomes to vascular-smooth muscle cells", J Artif Organs, 2011, vol. 14, No. 4, pp. 301-309.
Ise et al., "Vimentin and desmin possess GlcNAc-binding lectin-like properties on cell surfaces", Glycobiology, 2010, vol. 20, No. 7, pp. 843-864.
Kim et al., "Interactions of vimentin- or desmin-expressing liver cells with N-acetylglucosamine-bearing polymers", Biomaterials, 2012, 33, pp. 2154-2164.
Kobayashi et al., "Surface coating of bone marrow cells with N-acetylglucosamine for bone marrow implantation therapy", Biomaterials, 2009, 30, pp. 574-582.
Komura et al., "Dynamic behaviors of vimentin induced by interaction with GlcNAc molecules", Glycobiology, 2012, vol. 22, No. 12, pp. 1741-1759.

(Continued)

*Primary Examiner* — Micah Paul Young
(74) *Attorney, Agent, or Firm* — Birch, Stewart, Kolasch & Birch, LLP

(57) ABSTRACT

An N-acetylglucosamine sugar chain group-containing compound which can easily reach cells/sites on which a vimentin and/or desmin protein(s) is/are exposed, which compound has excellent affinity to N-acetylglucosamine sugar chain-recognizing proteins; a drug delivery carrier compound comprising the compound; a preparation using the drug delivery earner compound; and a drug delivery system; are provided. These are an N-acetylglucosamine sugar chain group-containing compound having a weight average molecular weight within the range of 15,000 to 100,000; a drug delivery carrier compound comprising the compound; a preparation using the drug delivery carrier compound; and a drug delivery system.

9 Claims, 4 Drawing Sheets

(56) References Cited

OTHER PUBLICATIONS

Nogawa et al., "Polyethylenimine/arabinogalactan conjugate as a hepatocyte specific gene carrier", S.T.P. Pharma Sciences, 2001, vol. 11, No. 1, pp. 97-102.
Written Opinion of the International Searching Authority, issued in PCT/JP2015/064344 (PCT/ISA/237), dated Aug. 25, 2015.
Yamazaki et al., "Preparation and Characterization of Neoglycoprotein-Liposome Conjugates: A Promising Approach to Developing Drug Delivery Materials Applying Sugar Chain Ligands", Trends in Glycoscience and Glycotechnology, May 2001, vol. 13, No. 71, pp. 319-329.
Chinese Office Action and Search Report, dated Apr. 3, 2018, for Chinese Application No. 201580026100.4.
Yin et al., "Coating chemistry," Aug. 1, 1997, p. 213 (Total pp. 3).

* cited by examiner

N-ACETYLGLUCOSAMINE SUGAR CHAIN GROUP-CONTAINING COMPOUND, CARRIER COMPOUND FOR DRUG DELIVERY, DRUG PREPARATION, AND DRUG DELIVERY SYSTEM

TECHNICAL FIELD

The present invention relates to an N-acetylglucosamine sugar chain group-containing compound, a drug delivery carrier compound, a preparation, and a drug delivery system. More specifically, the present invention relates to an N-acetylglucosamine sugar chain group-containing compound which can easily reach cells/sites on which a vimentin and/or desmin protein(s) is/are exposed, which compound has excellent affinity to N-acetylglucosamine sugar chain-recognizing proteins; a drug delivery carrier compound comprising the compound; a preparation using the carrier compound; and a drug delivery system.

BACKGROUND ART

Intervention treatment, in which a balloon or a stent is inserted into a blood vessel, and a narrowed portion is spread therewith, has been conventionally carried out for patients with ischemic heart diseases having a narrowed coronary artery due to arterial sclerosis or thrombus formation.

In this process, rubbing by the balloon or the stent may occur in the narrowed portion to cause detachment of vascular endothelial cells, causing injury of the portion. As a result, inflammation of the blood vessel, intimal hyperplasia due to abnormal growth of smooth muscle cells or cardiac muscle cells behind the endothelial cells at the injured site, or another thrombus formation, may occur to narrow the blood vessel again. Thus, a coil to which a sustained-release formulation of a drug for preventing inflammation, hypertrophy, or thrombosis is applied needs to be inserted into this site to prevent the restenosis and the like. This treatment is laborious, and imposes a heavy burden on the patient.

Fibrous disorders, such as those in which excessive fibrosis causes pathological disorders and tissue dysfunctions, are caused by abnormal accumulation of a fibrous tissue in a tissue. This fibrous tissue is generated also by disorder processes other than surgery, injury, and wounding, and examples of such processes include chronic disorders such as liver cirrhosis, hepatic fibrosis, glomerulonephritis, pulmonary fibrosis, scleroderma, myocardial fibrosis, fibrosis after myocardial infarction, central nervous system fibrosis after an attack or a neurodegenerative disorder (for example, Alzheimer's disease), proliferative vitreoretinopathy (PVR), restenosis (after, for example, angioplasty), and arthritides.

A simple system which enables specific delivery of these drugs to the heart, a blood vessel, or a site injured by fibrosis, for treatment of (that is, suppression or prevention of or recovery from) the symptoms described above has been demanded. As drug delivery systems, Non-patent Document 1 describes a complex of neoglycoprotein and liposome as a sugar chain-introduced drug delivery material, and Non-patent Document 2 describes a complex of polyethyleneimine and arabinogalactan, which is a gene delivery agent specific to hepatocytes. However, these do not have specific affinity to injured sites of the heart or blood vessels.

Use of a convertase inhibitor in production of pharmaceuticals for reducing cicatrization during wound healing, or for reducing fibrosis during treatment of fibrotic conditions, which convertase inhibitor is to be topically applied to the site of injury or fibrotic disorder, has been proposed (see Patent Document 1). In terms of drug delivery agents and the like, drug delivery agents on which a compound showing specific interaction with a particular protein such as vimentin or desmin present in cardiac muscle cells, vascular smooth muscle cells, skeletal myoblasts, and/or the like damaged by ischemia or the like, for example, N-acetylglucosamine, is exposed, and drug delivery agents in which N-acetylglucosamine is bound to the surface of colloid particles through avidins with which the surface is coated (see Patent Documents 2 and 3), have been proposed. A drug delivery system and the like using a drug delivery carrier compound having a first region having affinity to lipid membrane containing a drug therein, and a second region which binds to the first region and contains an automagnetic organic molecule (see Patent Document 4), have also been proposed.

RELATED ART DOCUMENTS

Patent Documents

Patent Document 1: JP 2005-535674 A (Claims and the like)
Patent Document 2: JP 2007-1923 A (Claims and the like)
Patent Document 3: JP 2009-46413 A (Claims and the like)
Patent Document 4: JP 2013-63926 A (Claims and the like)

Non Patent Documents

Non-patent Document 1: Noboru Yamazaki, Yoshifumi Jigami, Hans-Joachim Gabius, and Shuji Kojima, Trends in Glycoscience and Glycotechnology, Vol. 13. No. 71. pp. 319-329 (May 2001)
Non-patent Document 2: M. Nogawa, T. Ishihara, T. Akaike, and A. Maruyama, S.T.P. PharmaSciences, Vol. 11, No. 1, pp 97-102 (2001)

SUMMARY OF THE INVENTION

Problems to be Solved by the Invention

In the invention described in Patent Document 1, there is no method for delivering the convertase inhibitor to a predetermined site, so that direct application to the site or a method that allows the convertase inhibitor to reach the site directly as much as possible (for example, by use as an inhalant in cases of healing of a wound in the lung) is used. However, in this method, the administration of the convertase inhibitor is systemic administration rather than topical application. Since systemic administration of a convertase inhibitor is harmful, the method is not preferred. In the Patent Documents 2 and 3, N-acetylglucosamine is used as a drug delivery agent. However, since the drug hardly reaches cell/sites on which vimentin- or desmin-based N-acetylglucosamine-recognizing proteins are exposed, and, even if the drug reaches the cells/sites, the drug does not bind to, or hardly binds to, the N-acetylglucosamine sugar chain-recognizing proteins, so that the performance of the drug delivery agent is still not satisfactory.

In view of this, an object of the present invention is to provide an N-acetylglucosamine sugar chain group-containing compound which can easily reach cells/sites on which a vimentin and/or desmin protein(s) is/are exposed, which compound has excellent affinity to N-acetylglucosamine sugar chain-recognizing proteins; a drug delivery carrier compound comprising the compound; a preparation using the drug delivery carrier compound; and a drug delivery system.

Means for Solving the Problems

As a result of intensive study to solve the problems described above, the present inventor discovered that, by adjusting the weight average molecular weight of a compound having an N-acetylglucosamine sugar chain group to a particular range, the above problems can be solved, thereby completing the present invention.

That is, the N-acetylglucosamine sugar chain group-containing compound of the present invention is characterized in that it has a weight average molecular weight within the range of 15,000 to 100,000.

The N-acetylglucosamine sugar chain group-containing compound of the present invention is preferably a polymer.

The N-acetylglucosamine sugar chain group-containing compound of the present invention preferably has 27 to 175 N-acetylglucosamine sugar chain groups per molecule.

The N-acetylglucosamine sugar chain group-containing compound of the present invention is preferably a biotin compound.

In the N-acetylglucosamine sugar chain group-containing compound of the present invention, 3-mercaptopropionic acid is preferably bound to its terminus/termini.

The drug delivery carrier compound of the present invention is characterized in that it is composed of the N-acetylglucosamine sugar chain group-containing compound.

The preparation of the present invention is characterized in that the drug delivery carrier compound carries at least one agent selected from the group consisting of therapeutic agents, fluorescent agents, and contrast media, and the N-acetylglucosamine sugar chain group is exposed on the surface.

The drug delivery carrier compound of the present invention is characterized in that it is a colloidal particle in which the N-acetylglucosamine sugar chain group is exposed on the surface.

The preparation of the present invention is characterized in that the colloidal particle of the drug delivery carrier compound contains at least one agent selected from the group consisting of therapeutic agents, fluorescent agents, and contrast media.

The drug delivery system of the present invention is characterized in that it comprises: binding the N-acetylglucosamine sugar chain group-containing compound to the surface of at least one agent selected from the group consisting of therapeutic agents, fluorescent agents, and contrast media; and guiding the agent(s) to an affected area(s) of interest by the N-acetylglucosamine sugar chain group exposed on the surface.

The drug delivery system of the present invention is characterized in that it comprises: including, at least one agent selected from the group consisting of therapeutic agents, fluorescent agents, and contrast media in a colloidal particle having a surface to which the N-acetylglucosamine sugar chain group-containing compound is bound; and guiding the agent(s) in the colloidal particle to an affected area(s) of interest by the N-acetylglucosamine sugar chain group exposed on the surface.

Effects of the Invention

The present invention can provide an N-acetylglucosamine sugar chain group-containing compound which can easily reach cells/sites on which a vimentin and/or desmin protein(s) is/are exposed which compound has excellent affinity to N-acetylglucosamine sugar chain-recognizing proteins; a drug delivery carrier compound comprising the compound; a preparation using the drug delivery carrier compound; and a drug delivery system.

MODE FOR CARRYING OUT THE INVENTION

Figure 1:
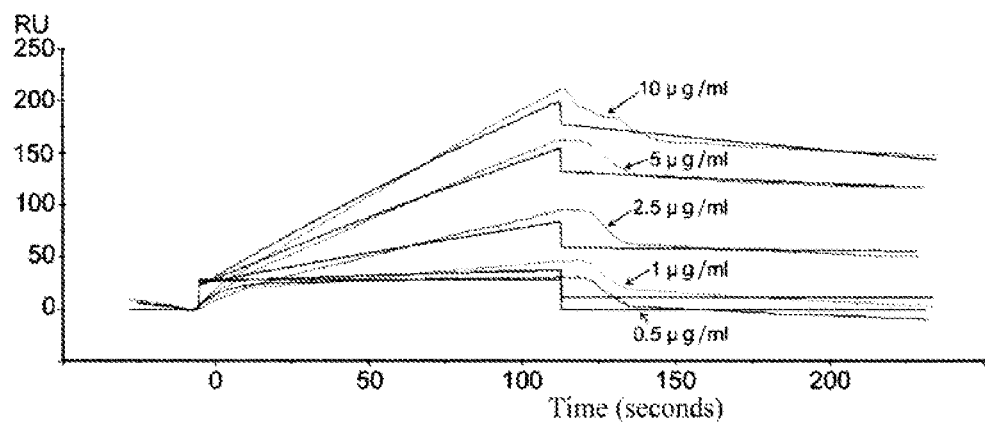
FIG. 1 is a sensorgram fix evaluation of binding, of the N-acetylglucosamine sugar chain group-containing compound of Comparative Example 2 to vimentin immobilized on a gold surface.

The N-acetylglucosamine sugar chain group-containing compound of the present invention is a compound characterized in that it has a weight average molecular weight within the range of 15,000 to 100,000, and has an N-acetylglucosamine sugar chain group. In cases where the weight average molecular weight is less than 15,000, the compound has low affinity to N-acetylglucosamine-recognizing proteins such as vimentin and desmin. In cases where the weight average molecular weight is more than 100,000, the ratio at which the agent reaches the desired cells/sites is low. The weight average molecular weight is preferably within the range of 16,000 to 50,000, more preferably within the range of 16,500 to 40,000, still more preferably within the range of 17,000 to 30,000 from the viewpoint of the ease of synthesis, the yield and the ratio at which the agent reaches the desired cells/sites. Conventionally, as an N-acetylglucosamine sugar chain group-containing compound a vinyl resin in which chitobiose is bound at an N-acetylglucosamine terminus has been used (see, for example, Example 1 in Patent Document 2), and its weight average molecular weight was about 120,000. Drug delivery agent colloids obtained by binding, to a carrier, an N-acetylglucosamine sugar chain group-containing compound obtained by binding of chitobiose and biotin (with a molecular weight of about 700) have also been used (see, for example, Example 13 in Patent Document 3).

In the N-acetylglucosamine sugar chain group-containing compound of the present invention, examples of the N-acetylglucosamine sugar chain group include an N-acetylglucosamine group; and chitopolyose groups in which two to six N-acetylglucosamine groups are linked together, that is a chitobiose group, chitotriose group, chitotetraose group, chitopentaose group, and chitohexaose group. In particular, an N-acetylglucosamine group and a chitobiose group are preferred, and a chitobiose group is more preferred.

As a specific example of the N-acetylglucosamine sugar chain group, the chemical formula of a chitobiose group is shown below, but the present invention is not limited thereto.

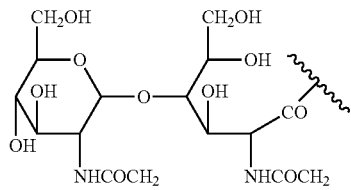

In the N-acetylglucosamine sugar chain group-containing compound of the present invention, the number of the N-acetylglucosamine sugar chain groups per molecule is preferably 27 to 175, more preferably 29 to 88, still more preferably 30 to 70, especially preferably 30 to 50.

The N-acetylglucosamine sugar chain group-containing compound of the present invention has an N-acetylglucosamine sugar chain group for allowing the compound to act on N-acetylglucosamine-recognizing proteins such as vimentin and desmin, and can be obtained by introducing an N-acetylglucosamine sugar chain group to a compound appropriately selected depending on the object. The compound of the present invention is more preferably a polymer obtained by polymerizing monomers having an N-acetylglucosamine sugar chain group, or as compound obtained by binding N-acetylglucosamine to as high molecular weight compound such as a polymer. The compound of the present invention is preferably a polymer.

The N-acetylglucosamine sugar chain group-containing compound of the present invention may have a hydrophobic group from the viewpoint of adsorption to the carrier.

The method for producing the N-acetylglucosamine sugar chain group-containing compound is not limited. Examples of the method for producing the polymer obtained by polymerizing monomers having an N-acetylglucosamine sugar chain group include a method wherein monomers in which a compound having a hydrophobic group such as a styrene compound is bound to the reducing end of an N-acetylglucosamine sugar chain are polymerized. More specifically, examples of the production method include a method wherein the amino group of vinylbenzylamine, which is a compound having a hydrophobic group, is subjected to reductive amination with chitobiose to obtain styrene-based monomers in which an N-acetylglucosamine group is introduced, and the resulting monomers are polymerized to produce the polymer. Examples of the method for producing the compound obtained by binding N-acetylglucosamine to a high molecular weight compound include a method wherein polyethyleneimine, which is a cationic polymer, or a polymer compound having a hydrophobic group, such as poly-L-lysine, is bound at the reducing end of the N-acetylglucosamine sugar chain.

Here, examples of the method for binding the N-acetylglucosamine sugar chain to the compound include, but are not limited to, binding of an amino group of a compound having the amino group to the reducing end of the N-acetylglucosamine sugar chain by reductive amination reaction. Alternatively, a hydroxyl group of the N-acetylglucosamine sugar chain may be substituted with a carboxyl group, and the carboxyl group may be bound to group of a compound having the amino group by 1-ethyl-3-(3-dimethylaminopropyl)carbodiimide (EDC) coupling or the like.

The method for polymerizing the monomers is not limited. For example, the polymer can be obtained by living radical polymerization or by a polymerization method using a chain transfer agent. More specifically, chitobiose as an N-acetylglucosamine sugar chain may be mixed with vinylbenzylphthalimide as a compound having a hydrophobic group at a molar ratio of 1:1 to produce monomers, and the resulting monomers may be subjected to radical polymerization in a solution in DMF, DMSO, water, or the like, to obtain poly[N-p-vinylbenzyl-O-2-acetamide-2-deoxy-β-D-glucopyranosyl-(1→4)-2-acetamide-2-deoxy-β-D-gluconamide] (PVGlcNAc). In the polymerization method using a chain transfer agent, a polymer having a controlled molecular weight can be produced by performing polymerization in which the mixing ratio of the chain transfer agent, such as mercaptopropionic acid, to the monomers is controlled.

The N-acetylglucosamine sugar chain group-containing compound of the present invention may be an N-acetylglucosamine sugar chain group-containing biotin compound. Production of the N-acetylglucosamine sugar chain group-containing biotin compound can be carried out by treating an N-acetylglucosamine sugar chain group-containing compound with a weak acid to produce an aldehyde group, and then reacting biotin having a hydrazine group therewith.

[Drug Delivery Carrier Compound]

The drug delivery carrier compound of the present invention is composed of the N-acetylglucosamine sugar chain group-containing compound of the present invention. The drug delivery carrier compound of the present invention may be constituted by the N-acetylglucosamine group-containing compound alone, or may be a compound in which the N-acetylglucosamine-sugar chain group-containing compound is bound to the surface of another material used for drug delivery such as a carrier, for example, a colloidal particle. Examples of the colloidal particle include metallic or inorganic particles such as particles of gold, platinum, silver, magnetic body, or ceramic; particles derived from a synthetic or natural product such as polyethylene glycol, polystyrene, acrylic resin, polylactic acid, polycaprolactone, polyhydroxyalkanoate, polyglycolic acid, modified polyvinyl alcohol, casein, modified starch or cellulose, or protein; and liposomes. The method for binding the N-acetylglucosamine sugar chain group-containing compound to the surface of the colloidal particle is not limited. For example, in cases where the colloidal particle is a gold particle, a thiol group may be introduced to an N-acetylglucosamine sugar chain group-containing compound, and the resulting compound may be covalently bound to the surface of the gold colloid, to allow binding of the compound to the surface of the particle. In cases of a polylactic acid, a solution in which an N-acetylglucosamine group-containing compound is dissolved may be mixed with the polylactic acid to coat the surface of the polylactic acid particle with the N-acetylglucosamine sugar chain group-containing compound, to allow binding of the compound to the surface of the particle. In cases of a liposome, the surface of the liposome may be coated with a compound prepared by introducing an alkyl group to an N-acetylglucosamine sugar chain group-containing compound, to allow binding of the compound to the surface of the liposome.

The particle size of the colloidal particle is preferably within the range of 5 to 800 nm in terms of the mass average particle size. In cases where the particle size is less than 5 nm, the N-acetylglucosamine group-containing compound can be hardly bound to the particle, and particles to which the N-acetylglucosamine group is not added are quickly excreted from the body, which is not preferred. In cases where the particle size exceeds 800 nm, the particles are eliminated as a foreign substance from the body by macrophages and the like, which is not preferred. From the viewpoint of the load performance of the N-acetylglucosamine group on the particle surface, and the drug delivery performance, the particle size is preferably within the range of 7 to 500 nm, especially preferably within the range of 10 to 300 nm. By controlling the particle size within this range, the particles can be made to reach, selectively and efficiently, gaps generated between cells in sites of vascular injury, or cells such as smooth muscle cells or sites that are exposed in blood vessels, so that the particles can be easily incorporated into the cells/sites.

[Preparation]

A preparation of the present invention is characterized in that the drug delivery carrier compound carries at least one agent selected from the group consisting of therapeutic agents, fluorescent agents, and contrast media, and the N-acetylglucosamine sugar chain group is exposed on the surface. Another preparation of the present invention is characterized in that the drug delivery carrier compound is a colloidal particle in which the N-acetylglucosamine sugar chain group is exposed on the surface, which colloidal particle contains at least one agent selected from the group consisting of therapeutic agents, fluorescent agents, and contrast media. These preparations of the present invention reach cells/sites on which an N-acetylglucosamine sugar chain-recognizing protein(s) such as vimentin and/or desmin is/are exposed, through blood circulation. Thereafter, the N-acetylglucosamine sugar chain group of the drug delivery carrier compound and the N-acetylglucosamine sugar chain-recognizing protein interact with each other to attract each other, allowing attachment of the preparation to, or penetration of the preparation into, the cells. The agent(s) is/are then released from the preparation by exudation, and absorbed into the cells, followed by allowing production of fluorescence, contrast imaging, or production of a pharmacological effect(s).

Examples of the fluorescent agents include fluorescein isothiocyanate (FITC) and a living-cell staining dye Calcein-AM (trade name; manufactured by Dojindo Laboratories). Examples of the contrast media include gadolinium compounds for nuclear magnetic resonance imaging. Examples of the therapeutic agents include vascular endothelial growth promoters, vascular smooth muscle cell growth inhibitors, anti-inflammatory drugs, anticancer drugs, and antirheumatic chugs.

[Drug Delivery System]

A drug delivery system of the present invention is characterized in that it comprises: binding the compound of the present invention to the surface of at least one agent selected from the group consisting of fluorescent agents, contrast media, and therapeutic agents; and guiding the agent(s) to an affected area(s) by the N-acetylglucosamine sugar chain group exposed on the surface. Another drug delivery system of the present invention is characterized in that at least one agent selected from the group consisting of therapeutic agents, fluorescent agents, and contrast media is included in a colloidal particle having a surface to which the compound of the present invention is bound; and the agent(s) included in the colloidal particle is/are guided to an affected area(s) of interest by the N-acetylglucosamine sugar chain group exposed on the surface.

Since the N-acetylglucosamine sugar chain group-containing compound, the drug delivery carrier compound, the agent using the drug delivery carrier compound, and the drug delivery system, of the present invention allow an agent to reach desired cells/sites (cells/sites on which a vimentin and/or desmin protein(s) is/are exposed) more efficiently than conventional drug delivery systems, the agent can be allowed to reach the desired sites efficiently even in cases where the amount of the agent is smaller than those in conventional drug delivery systems, so that a higher effect of the agent can be obtained as a result. Thus, the N-acetylglucosamine sugar chain group-containing compound, the deism delivery carrier compound, the preparation, and the drug delivery system, of the present invention are effective in the field of medicine, in particular, for tests, diagnoses, and treatments.

EXAMPLES

The present invention is described below in more detail by way of Examples, but the present invention is not limited to these Examples.

(Preparation of Monomers)

Chitobiose (0.5 g) was dissolved in methanol (20 mL), and 1.425 g of iodine was added to the resulting solution. To the resulting mixture, 4% KOH was added dropwise until the brown color of the iodine disappeared. Thereafter, recrystallization was performed using diethyl ether, and the crystallized product was dissolved in water, followed by purification of chitobionic acid using an ion-exchange resin (Amberlite IR120). Condensation of the chitobionic acid was carried out using vinylbenzylamine together with WSC (water-soluble carbodiimide). The prepared monomers were purified by precipitation using chloroform. The resulting precipitate was dissolved in water, and subjected to freeze-drying.

Comparative Example 1: Preparation of N-Acetylglucosamine Sugar Chain Group-Containing Compound (PV-GlcNAc; Weight Average Molecular Weight, 9300)

With 0.185 mmol of the monomers obtained as described above, 0.00185 mmol of 3-mercaptopropionic acid (MPA), and azobisisobutyronitrile (AIBN) in an amount in which the final concentration became 0.5%, were mixed, and the resulting mixture was dissolved in 500 μL of dimethylsulfoxide (DMSO). The resulting solution was incubated in an oil bath at 65° C. for 18 hours to allow polymerization. Thereafter, the resulting product was dissolved in water, and subjected to dialysis for one day and night. Subsequently, freeze-drying was carried out.

Comparative Example 2: Preparation of N-Acetylglucosamine Sugar Chain Group-Containing Compound (PV-GlcNAc; Weight Average Molecular Weight, 11,000)

With 0.185 mmol of the monomers obtained as described above, 0.0009 mmol of MPA, and AIBN in an amount in which the final concentration became 0.5%, were mixed, and the resulting mixture was dissolved in 500 µL of DMSO. The resulting solution was incubated in an oil bath at 65° C. for 18 hours to allow polymerization. Thereafter, the resulting product was dissolved in water, and subjected to dialysis for one day and night. Subsequently, freeze-drying was carried out.

Comparative Example 3: Preparation of N-Acetylglucosamine Sugar Chain Group-Containing Compound (PV-GlcNAc; Weight Average Molecular Weight, 14,000)

With 0.185 mind of the monomers obtained as described above, 0.00037 mmol of MPA, and AIBN in an amount in which the final concentration became 0.5%, were mixed, and the resulting mixture was dissolved in 500 µL of DMSO. The resulting solution was incubated in an oil bath at 65° C. for 18 hours to allow polymerization. Thereafter, the resulting product was dissolved in water, and subjected to dialysis for one day and night. Subsequently, freeze-drying was carried out.

Example 1: Preparation of N-Acetylglucosamine Sugar Chain Group-Containing Compound (PV-GlcNAc; Weight Average Molecular Weight, 17,000)

With 0.185 mmol of the monomers obtained as described above, 0.000185 mmol of MPA, and AIBN in an amount in which the final concentration became 0.5%, were mixed, and the resulting mixture was dissolved in 500 µL of DMSO. The resulting solution was incubated in an oil bath at 65° C. for 18 hours to allow polymerization. Thereafter, the resulting product was dissolved in water, and subjected to dialysis for one day and night. Subsequently, freeze-drying was carried out.

Comparative Example 4: Preparation of N-Acetylglucosamine Sugar Chain Group-Containing Compound (PV-GlcNAc; Weight Average Molecular Weight, 120,000)

With 0.185 mmol of the monomers obtained as described above, AIBN was mixed in an amount in which the final concentration became 0.5%, and the resulting mixture was dissolved in 500 µL of DMSO. The resulting solution was incubated in an oil bath at 65° C. for 18 hours to allow polymerization. Thereafter, the resulting product was dissolved in water, and subjected to dialysis for one day and night. Subsequently, freeze-drying was carried out.

Measurement of physical property values and evaluation of various properties were carried out by the methods described below. The obtained results are shown in Table 1.

(1) Interaction with N-Acetylglucosamine Sugar Chain-Recognizing Protein (Vimentin)

A recombinant protein of the N-acetylglucosamine-binding domain of vimentin was immobilized on a sensor chip, and interactions of the N-acetylglucosamine sugar chain group-containing compounds with vimentin were studied by surface plasmon resonance analysis using BIACORE-J, manufactured by GE Healthcare. The sensorgrams obtained were observed for judging the relative levels of interaction based on visual comparison of the maximum values in the sensorgrams.

(2) Dissociation Constant ($K_D$ (M))

A five-step concentration series (with the five kinds of concentrations 0.5 µg/ml, 1 µg/ml, 2.5 µg/ml, 5 µg/ml, and 10 µg/ml) of each N-acetylglucosamine sugar chain group-containing compound was provided. Binding (intermolecular interaction) between vimentin immobilized on a gold surface and the N-acetylglucosamine sugar chain group-containing compound provided was studied using BIACORE-J, manufactured by GE Healthcare. From the results based on the sensorgram for each concentration, the dissociation constant of each N-acetylglucosamine sugar chain group-containing compound was calculated. The results based on the sensorgrams for Comparative Example 2, Comparative Example 3, Example 1, and Comparative Example 4 are shown in FIGS. 1 to 4, respectively (no measurement was carried out for 0.5 µg/ml in Comparative Example 3). The ordinate represents the resonance unit, and abscissa represents the time (seconds). These diagrams show reactivities of the compounds at various concentrations to vimentin. As the concentration increased, the reactivity increased. Until Second 120 (or Second 60, in the cases of Comparative Examples) as counted from the time point when the N-acetylglucosamine sugar chain group-containing; compound was reacted with vimentin, the data reflect binding of the compound to vimentin. The data after Second 120 (Or Second 60, in the cases of Comparative Examples) reflect dissociation of the N-acetylglucosamine sugar chain group-containing compound from vimentin. From these reaction processes, the dissociation constant was calculated. In Comparative Example 2, changes could be hardly found for 0.5 µg/ml, so that this condition was excluded from the calculation of the dissociation constant.

(3) Interaction with FITC-PV-GlcNAc

To 500 µL of a 5×10⁵ cells/mL HeLa cell suspension, an FITC-labeled N-acetylglucosamine sugar chain group-containing compound (FITC-PV-GlcNAc) was added at 4 µg/mL, and the reaction was allowed to proceed. The reaction was carried out at 4° C. for 30 minutes. Subsequently, centrifugation was carried out, followed by resuspending the cells in PBS. The stained cells were analyzed by flow cytometry using a flow cytometer (GUAVA easyCyte, manufactured by Millipore) to study staining of the HeLa cells with FITC-PV-GlcNAc. The results based on the flow cytometry for Comparative Example 1, Comparative Example 2, Comparative Example 3, Example 1, and Comparative Example 4 are shown in FIGS. 5 to 9, respectively. The ordinate represents the number of cells, and the abscissa represents the fluorescence intensity. Each filled histogram represents a histogram obtained by reacting FITC-PV-MA as a negative control, and each open histogram represents a HeLa cell population reacted with FITC-PV-GlcNAc.

(4) Weight Average Molecular Weight

The weight average molecular weight of each material was measured using a high-speed GPC apparatus (manufactured by Tosoh Corporation; HLC-8220GPC) under the following conditions. As columns, TSKgel G6000PWxL-CP+G5000PWxL-CP+3000PWxL-CP were used. As an eluent, 200 mM sodium nitratelacetonitrile=80/20 was used. The flow rate was 1 mL/min. An RI detector was used as a detector. The column temperature was 40° C. A standard curve for the molecular weight was prepared using

TABLE 1

Figure 2:
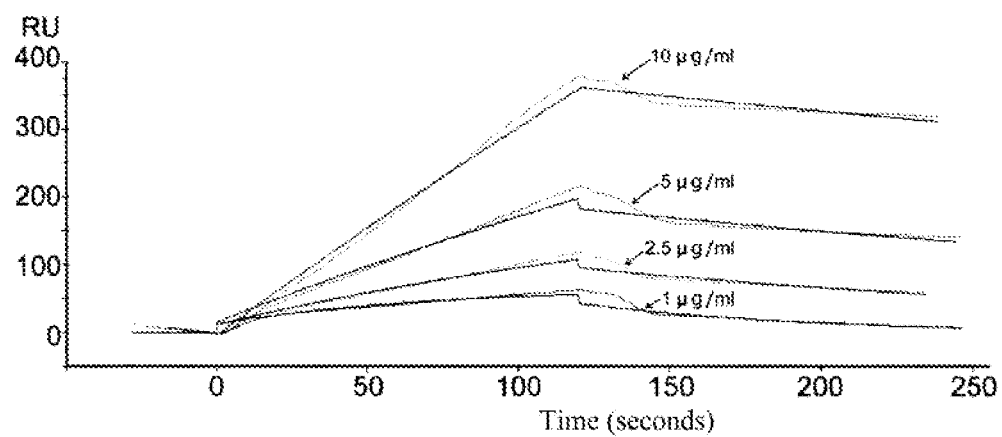
FIG. 2 is a sensorgram fix evaluation of binding of the N-acetylglucosamine sugar chain group-containing compound of Comparative Example 3 to vimentin immobilized on a gold surface.
Figure 3:
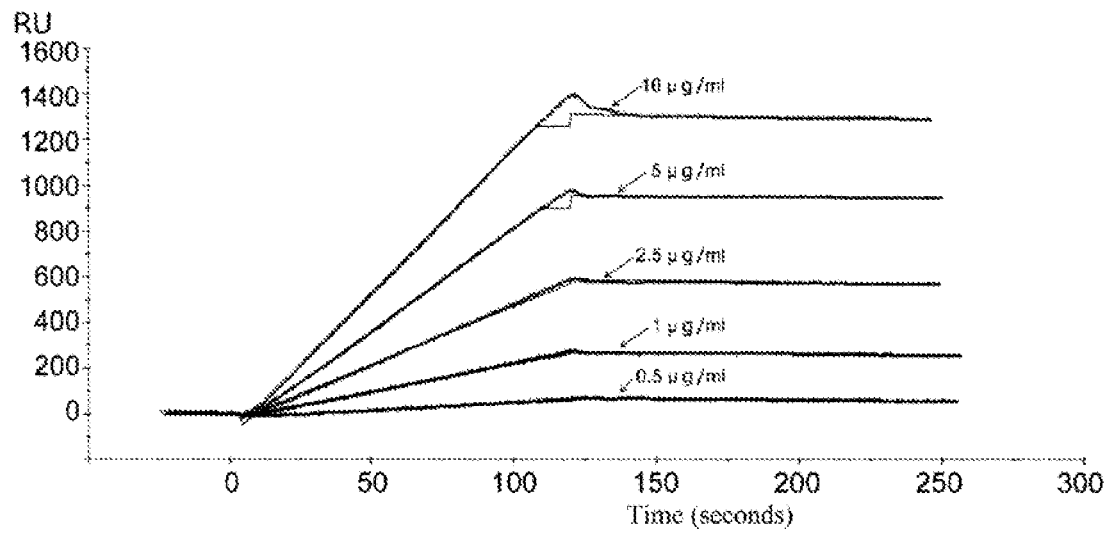
FIG. 3 is a sensorgram for evaluation of binding of the N-acetylglucosamine sugar chain group-containing compound of Example 1 to vimentin immobilized on a gold surface.
Figure 4:
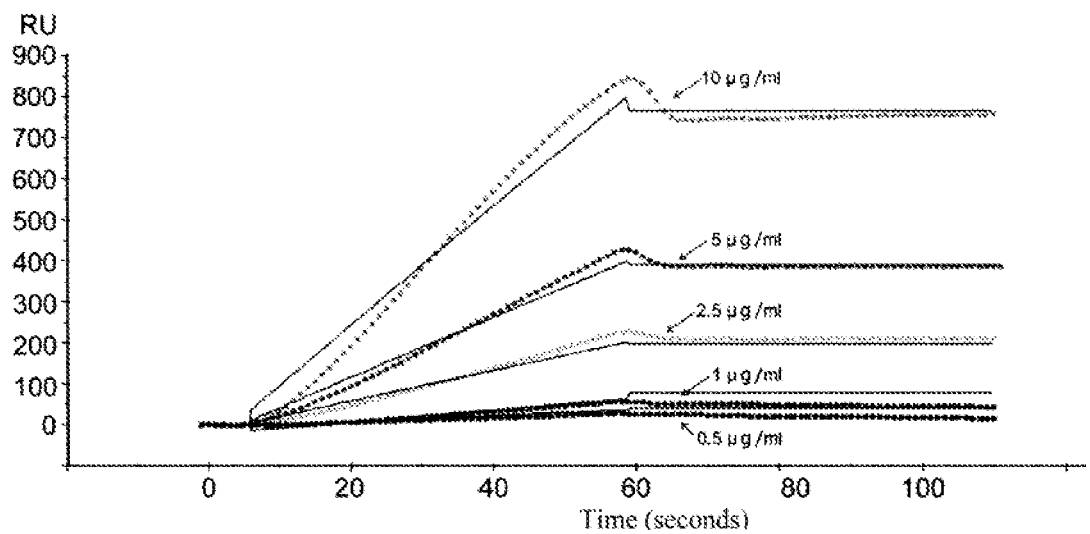
FIG. 4 is a sensorgram for evaluation of binding of the N-acetylglucosamine sugar chain group-containing compound of Comparative Example 4 to vimentin immobilized on a gold surface.
Figure 5:
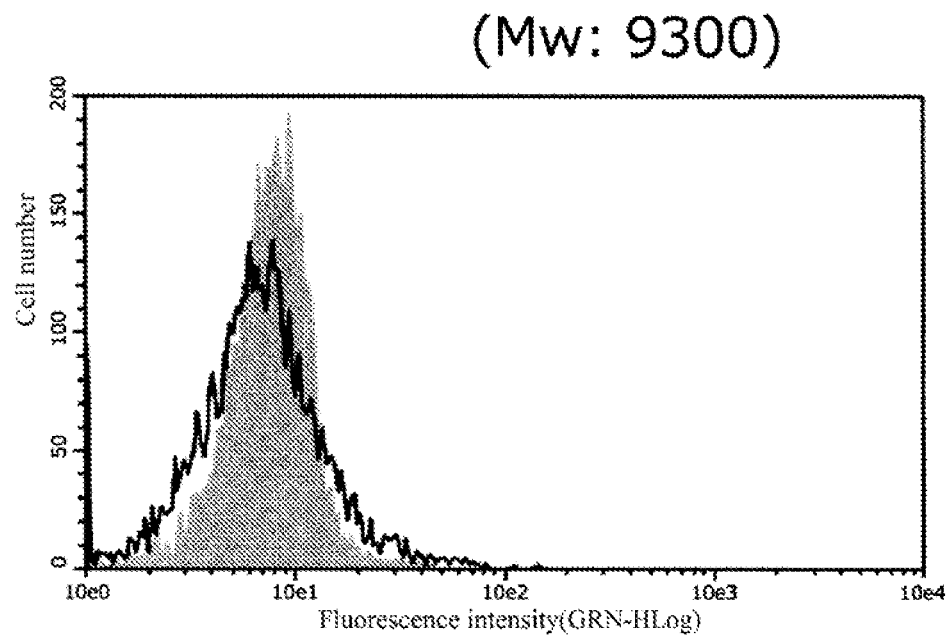
FIG. 5 is a graph showing the staining intensity of HeLa cells treated with an FITC-labeled product of the N-acetylglucosamine sugar chain group-containing compound of Comparative Example 1.
Figure 6:
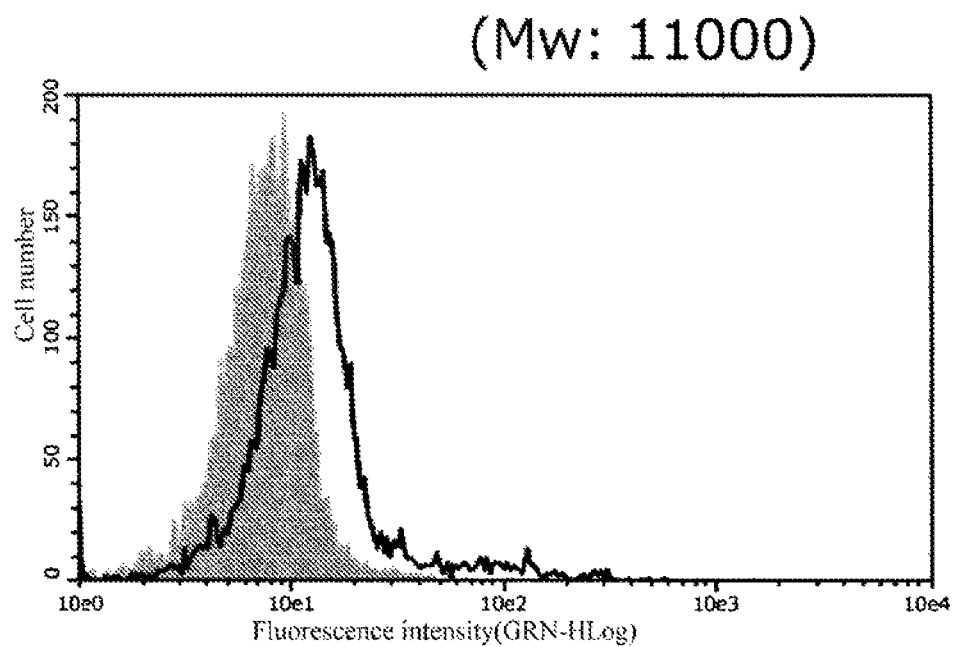
FIG. 6 is a graph showing the staining intensity of HeLa cells treated with an FITC-labeled product of the N-acetylglucosamine sugar chain group-containing compound of Comparative Example 2.
Figure 7:
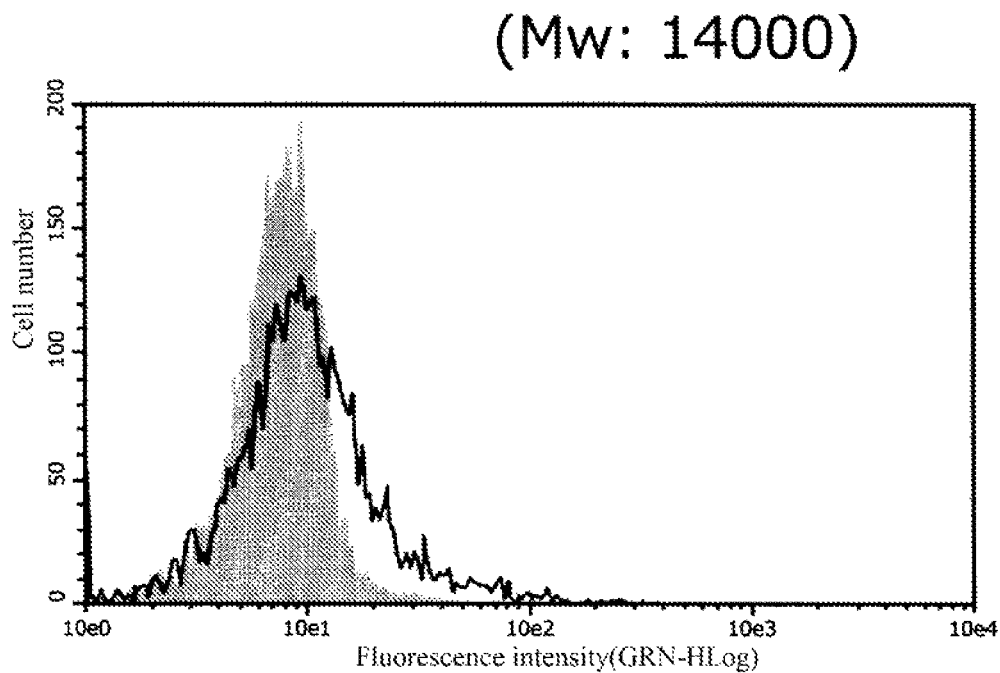
FIG. 7 is a graph showing the staining intensity of HeLa cells treated with an FITC-labeled product of the N-acetylglucosamine sugar chain group-containing compound of Comparative Example 3.
Figure 8:
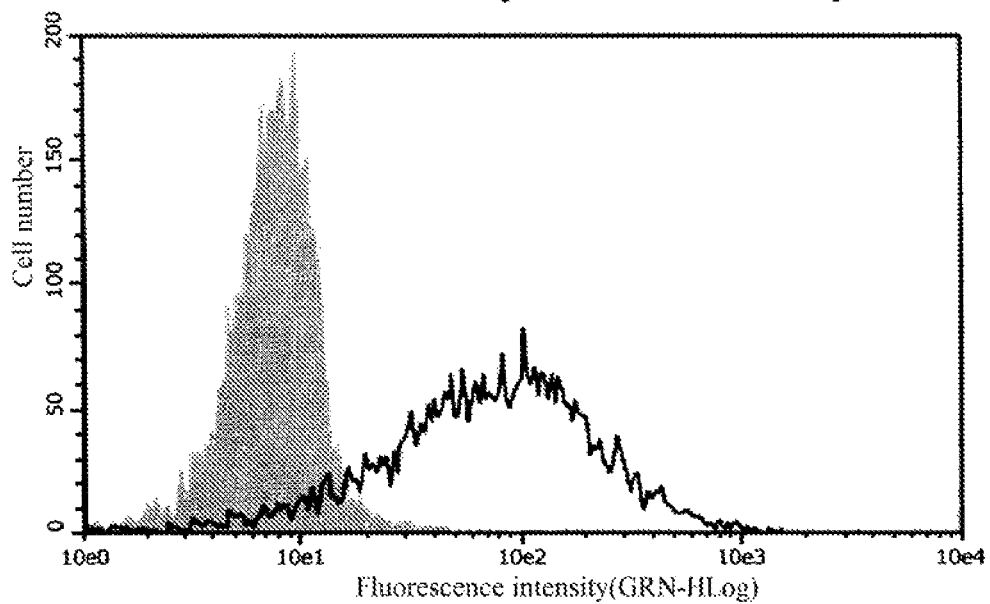
FIG. 8 is a graph showing the staining intensity of HeLa cells treated with an FITC-labeled product of the N-acetylglucosamine sugar chain group-containing compound of Example 1.
Figure 9:
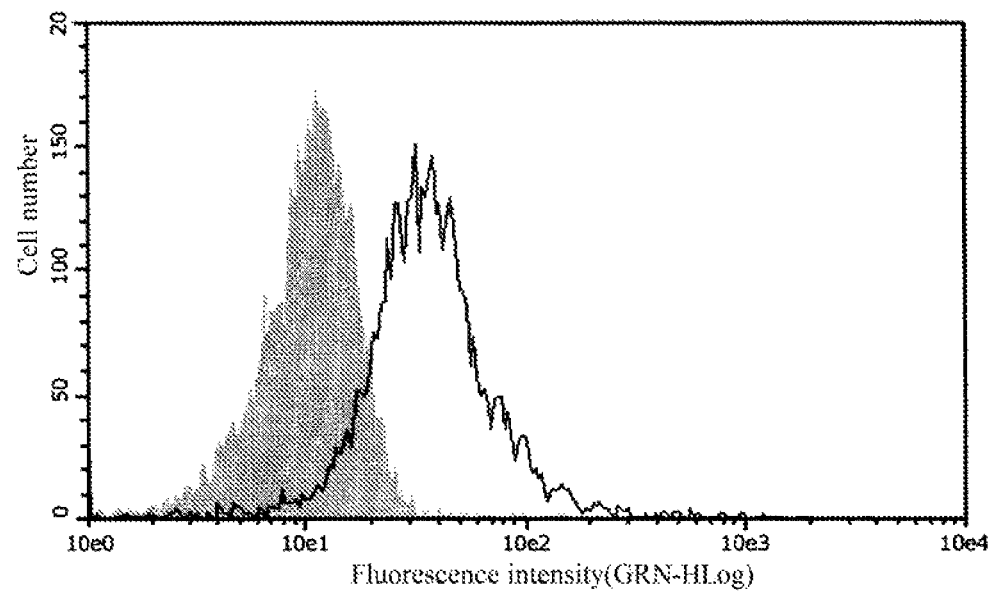
FIG. 9 is a graph showing the staining intensity of HeLa cells treated with an FITC-labeled product of the N-acetylglucosamine sugar chain group-containing compound of Comparative Example 4.

| | Comparative Example 1 | Comparative Example 2 | Comparative Example 3 | Example 1 | Comparative Example 4 |
|---|---|---|---|---|---|
| Sensorgram | + | + | ++ | +++++ | +++++ |
| Dissociation constant for vimentin ($K_D$ (M)) | – | $2.54 \times 10^{-6}$ FIG. 1 | $9.74 \times 10^{-6}$ FIG. 2 | $1.11 \times 10^{-10}$ FIG. 3 | $4.45 \times 10^{-10}$ FIG. 4 |
| Interaction of FITC-PV-GlcNAc | FIG. 5 | FIG. 6 | FIG. 7 | FIG. 8 | FIG. 9 |
| Weight average molecular weight | 9,300 | 11,000 | 14,000 | 17,000 | 120,000 |

In the table, "–" means an unmeasurable state.

From these results, it can be seen that the N-acetylglucosamine sugar chain group-containing compound of the Example has excellent interaction with the N-acetylglucosamine sugar chain-recognizing protein, and that this compound can easily reach the N-acetylglucosamine sugar chain-recognizing protein in the HeLa cells. Thus, it can be seen that, by a drug delivery agent carrier using the N-acetylglucosamine sugar chain group-containing compound of the present invention, a drug can be selectively allowed to reach desired cells or sites. It can further be seen that, by a drug delivery system using the compound of the present invention, a drug can be efficiently allowed to reach desired cells/sites.

The invention claimed is:

1. A drug delivery carrier compound comprising:
   a compound comprising N-acetylglucosamine sugar chain group with a weight average molecular weight within a range of 15,000 to 100,000,
   wherein the compound is a polymer,
   wherein 3-mercaptopropionic acid is bound to the polymer terminus/termini, and
   wherein said drug delivery carrier compound is a colloidal particle in which said N-acetylglucosamine sugar chain group is exposed on the surface of said colloidal particle.

2. The drug delivery carrier compound according to claim 1, wherein the compound has 27 to 175 N-acetylglucosamine sugar chain groups per molecule.

3. The drug delivery carrier compound according to claim 1, wherein the compound is a biotin compound.

4. A preparation comprising the drug delivery carrier compound according to claim 1, wherein said drug delivery carrier compound carries at least one agent selected from the group consisting of therapeutic agents, fluorescent agents, and contrast media, and said N-acetylglucosamine sugar chain group is exposed on the surface.

5. A preparation comprising the drug delivery carrier compound according to claim 1, wherein said colloidal particle contains at least one agent selected from the group consisting of therapeutic agents, fluorescent agents, and contrast media.

6. A drug delivery system comprising:
   binding the compound of the drug delivery carrier compound according to claim 1 to the surface of at least one agent selected from the group consisting of therapeutic agents, fluorescent agents, and contrast media; and
   guiding said agent(s) to an affected area(s) of interest by said N-acetylglucosamine sugar chain group exposed on the surface.

7. A drug delivery system comprising:
   including at least one agent selected from the group consisting of therapeutic agents, fluorescent agents, and contrast media in a colloidal particle having a surface to which the compound of the drug delivery carrier compound according to claim 1 is bound; and
   guiding said agent(s) in said colloidal particle to an affected area(s) of interest by said N-acetylglucosamine sugar chain group exposed on the surface.

8. A drug delivery system comprising:
   binding the compound of the drug delivery carrier compound according to claim 2 to the surface of at least one agent selected from the group consisting of therapeutic agents, fluorescent agents, and contrast media; and
   guiding said agent(s) to an affected area(s) of interest by said N-acetylglucosamine sugar chain group exposed on the surface.

9. A drug delivery system comprising:
   binding the compound of the drug delivery carrier compound according to claim 3 to the surface of at least one agent selected from the group consisting of therapeutic agents, fluorescent agents, and contrast media; and
   guiding said agent(s) to an affected area(s) of interest by said N-acetylglucosamine sugar chain group exposed on the surface.

* * * * *